United States Patent [19]
Wyler et al.

[11] 3,933,148
[45] Jan. 20, 1976

[54] DEVICE FOR DETERMINING SKIN SENSITIVITY

[75] Inventors: Eugen Wyler, Kusnacht; Wladimir Tur, Mutschellen, both of Switzerland

[73] Assignee: Lovida AG, Oberwil near Zug, Switzerland

[22] Filed: Apr. 12, 1974

[21] Appl. No.: 460,462

[30] Foreign Application Priority Data
Apr. 16, 1973 Switzerland.................... 5483/73

[52] U.S. Cl..................... 128/2 R; 73/81; 128/2 W
[51] Int. Cl.²........................................... A61B 10/00
[58] Field of Search............ 128/2 R, 2 N, 2 S, 2 T, 128/2 W; 73/81

[56] References Cited
UNITED STATES PATENTS

| 1,842,323 | 1/1932 | Gluzek | 73/81 X |
|---|---|---|---|
| 2,323,925 | 7/1943 | Markwardt | 73/81 |
| 2,704,539 | 3/1955 | Fisher | 128/2 N |
| 3,498,120 | 3/1970 | MacMillan | 73/81 X |
| 3,618,371 | 11/1971 | Martin | 73/81 X |
| 3,680,545 | 8/1972 | Miller | 128/2 N |
| 3,745,989 | 7/1973 | Pinna | 128/2 R |
| 3,805,599 | 4/1974 | Illman et al. | 73/81 |

*Primary Examiner*—Kyle L. Howell
*Attorney, Agent, or Firm*—Browdy and Neimark

[57] ABSTRACT

A device for determining the degree of skin sensitivity on the basis of the persistance of a streak. At least one element is provided which is to be compressed against the action of an elastic system or a spring. The outer end of this pressure element is provided with a surface which is contacted with the skin to enable a standardized pressure to be applied thereto.

6 Claims, 5 Drawing Figures

3,933,148

DEVICE FOR DETERMINING SKIN SENSITIVITY

BACKGROUND OF THE INVENTION

It is known that a red streak remains on the skin after irritating it with an object such as a fingernail, spoon handle, or laboratory spatula. The degree of redness or persistence duration is used as a basis for skin sensitivity. This rough method has the disadvantage, however, of yielding different results since the local pressure of the mechanical action varies considerably, depending on the investigator, the pressure applied and the object used.

A fine gradation of the degree of skin sensitivity or a reproducible standardized determination of the readiness of the skin to react to mechanical stimulation has not as yet been possible. This property of the skin is of particular importance, especially for skin property valuation, and thus a method to provide a standardized pressure to the skin must be found.

In dermatology and cosmetics, it is desirable to have a simple means for evaluating skin sensitivity. The purpose of this invention is to create such a device. This is accomplished according to the invention, by the fact that at least one pressure element projecting from a base is provided. This element is compressible into the base of the device, against the action of an elastic system or a spring element with a known spring force. The outer end of the pressure element is provided with an rough surface whose area is directly proportional to the spring tension and whose roughness is inversely proportional to the spring tension.

By this means, very accurate determinations of skin sensitivity can be made since the skin is always subjected to exactly the same definite pressure. Further features and advantages of the invention will be evident from the following description and from the claims.

SUMMARY OF THE INVENTION

A principle object of the present invention is to provide a device which overcomes the defects of the prior art, such as indicated above.

Another object is to provide a device for accurately measuring the sensitivity of the skin utilizing a standardized pressure element.

A further object is to provide a device for measuring the sensitivity of the skin where the pressure elements are compressed into its base against the action of an elastic system or spring element.

The device is placed upon the skin to be tested in such fashion that the spring-loaded pressure rod is pushed down into the housing at a definite and constant application pressure. A sweep is then made across the skin at the point on the skin (preferably on the inside of the forearm) to be tested. A red streak shows up after a short time; its persistence provides a criterion of the degree of sensitivity of the skin. If the streak produced by the device described above is, for example, still clearly and obviously visible after more than 10 minutes, the skin is judged to be sensitive. If the red streak has faded or can be seen only dimly after 10 minutes have elapsed, the skin is rated insensitive.

Any other pressure element can be provided instead of the pressure rod, which can be tensioned by an elastic system or by any spring element, such as lamellar, rubber, or gas-spring systems, or hydraulic, or pneumatic spring systems. The contact or sliding surface of the pressure element can also have any rounded shape, and in addition, instead of the adjusting screw, any other device can be provided to adjust the spring tension. In particular, a click-stop adjustment device can be provided with several adjustment steps such as "weak," "medium" and "strong."

According to a further embodiment of the invention, the device can contain several pressure elements. If these pressure elements have different spring tensions, or if they are provided with contact surfaces of different size or degree of roughness, after a certain time interval a precise statement can be made regarding the degree of skin sensitivity after all the rods in the device have been drawn simultaneously over the skin.

BRIEF DESCRIPTION OF THE DRAWING

The following sample embodiments of the invention are shown in greater detail in the drawings.

DETAILED DESCRIPTION OF THE DRAWING

Figure 1:
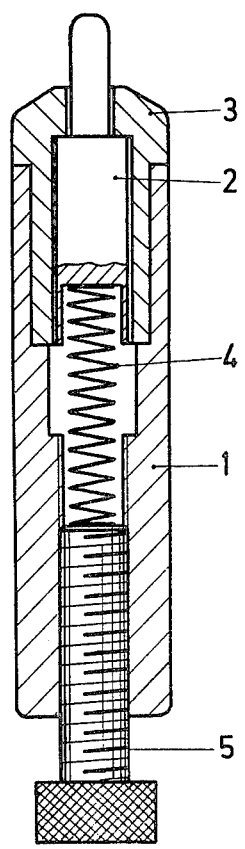
FIG. 1 shows an elevational view, partly in cross-section, through a first sample embodiment.

According to FIG. 1, an axially displacable pressure rod 2 is located in a housing 1, said rod being limited in its outward travel by a stop 3 connected to the housing. A coil spring 4 is located internally in a recess in the pressure rod, said spring pressing either directly on the housing or, as shown in FIG. 1, on an adjusting screw 5. The tension of the spring 4 can be adjusted by means of an adjusting screw 5 that is operable by a disc with a knurled edge. To ensure reproducible setting of the spring tension, a scale can be provided on the housing 1 or on the adjusting screw, the desired spring tension being readable from said scale.

Figure 2:
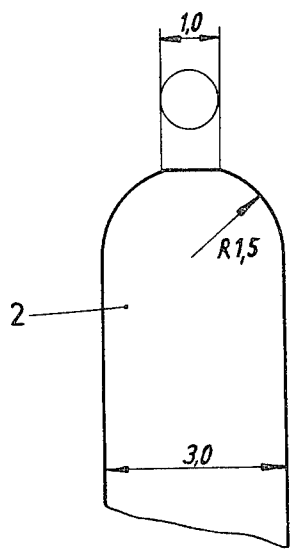
FIG. 2 shows the tip of the pressure rod in the device according to FIG. 1.

FIG. 2 shows the tip of the pressure rod in enlarged form, which in this example has a diameter of 3 mm, is rounded off to a radius of 1.5 mm, and flattened at the tip to a diameter of approximately 1 mm. The pressure rod is preferably made of a polyamide, however any other material may be used. Given the above dimensions for the pressure rod, the tension of the spring 4 should preferably be between 200 and 400 grams. This calculates to a spring pressure of 250-500 gm/mm$^2$ when the tip of the pressure rod is depressed to the base surface of the housing.

Figure 3:
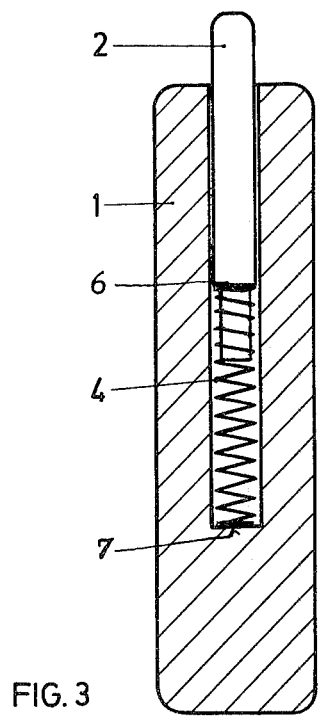
FIG. 3 shows an elevational view, partly in cross-section, of a second sample embodiment.

According to a simplified embodiment shown in FIG. 3, the pressure rod 2 is installed directly into the housing without the use of a stop. One end of the spring 4 is connected at a junction 6, and the other end is fastened directly to the housing 1.

Figure 4:
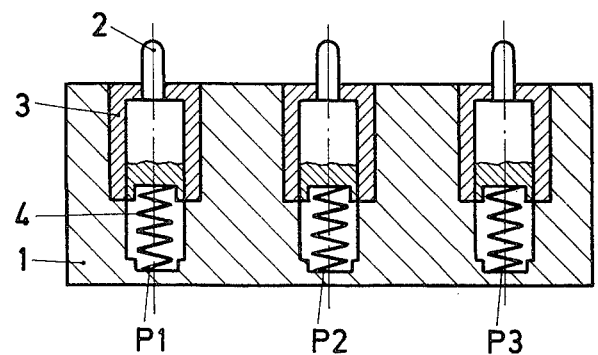
FIG. 4 shows an elevational view, partly in cross-section, of a third sample embodiment.
Figure 5:
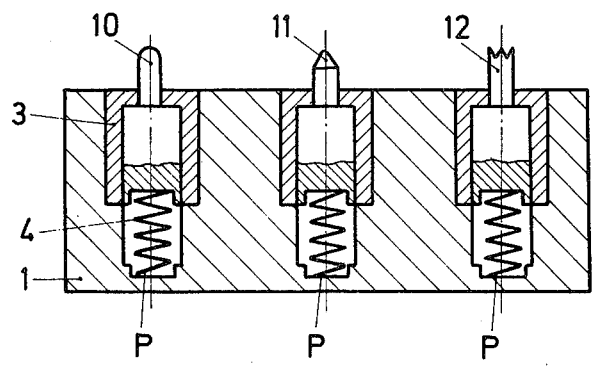
FIG. 5 shows an elevational view, partly in cross-section, of a fourth sample embodiment.

FIG. 4 shows a sample embodiment with three pressure rods, tensioned with different spring tensions P1, P2 and P3. FIG. 5 shows three pressure rods tensioned with the same spring tension P, but the surfaces of the pressure rods have different shapes. Pressure rod 10 is rounded, pressure rod 11 is conical and pressure rod 12 has a serrated surface. Pressure rod 12 will produce more of a skin irritation than the other two pressure rods, with rod 10 producing the least skin irritation of the three. All of the pressure elements may also have the same type of surface, but be provided with different surface roughnesses.

It will be obvious to those skilled in the art that various changes may be made without departing from the scope of the invention and the invention is not to be considered to what is shown in the drawings and described in the specification.

What is claimed is:

1. A device for determining the degree of skin sensitivity due to the persistence of a scratch trace on the skin surface produced by said device, comprising:
   a housing having a base surface;
   at least one pressure element having one end extending into said housing and having a rounded trace producing surface on the other end thereof, said trace producing surface protruding from said housing at said base surface;
   compressible means within said housing in engagement with said pressure element, having a predetermined spring force, for compressing said at least one pressure element against the skin surface at a constant pressure of 250–500 gm/mm$^2$ when said trace producing surface is depressed to said base surface,
   whereby said at least one pressure element is depressable into said housing at a constant pressure and therefore the pressure on the skin surface will be constant, thereby allowing a plurality of scratch traces to be applied to the skin surface at the same surface pressure.

2. Device according to claim 1, further including an adjusting means connected to said compression means for adjusting the tension of said compression means.

3. Device according to claim 1, wherein a plurality of pressure elements are provided projecting from said base surface, said elements being tensioned with different spring forces and being provided with similar outer surfaces.

4. Device according to claim 1, wherein a plurality of pressure elements are provided, projecting from said base surface, said elements being tensioned with the same spring tension and provided with different outer surfaces.

5. Device according to claim 1, wherein the trace producing surface of the pressure element is in the form of a rod having a diameter of approximately 3 mm and a rounded tip with a radius of 1.5 mm, having a flattened cap 1 mm in diameter.

6. Device according to claim 5, wherein the trace producing surface of the pressure element is made of a polyamide.

* * * * *